United States Patent
Rajamannan

(10) Patent No.: US 8,003,570 B2
(45) Date of Patent: Aug. 23, 2011

(54) COMPOSITION AND METHOD FOR KILLING NEMATODES AND WEEDS IN SOILS

(75) Inventor: A. Harry J. Rajamannan, Minneapolis, MN (US)

(73) Assignee: Agro-K Corporation, Minneapolis, MN (US)

( * ) Notice: Subject to any disclaimer, the term of this patent is extended or adjusted under 35 U.S.C. 154(b) by 1346 days.

(21) Appl. No.: 11/581,267

(22) Filed: Oct. 16, 2006

(65) Prior Publication Data

US 2008/0090730 A1    Apr. 17, 2008

(51) Int. Cl.
*A01N 47/28*    (2006.01)
*A01N 41/10*    (2006.01)

(52) U.S. Cl. .................................. 504/148; 514/711

(58) Field of Classification Search .................. None
See application file for complete search history.

(56) References Cited

U.S. PATENT DOCUMENTS

| 7,343,874 | B2 * | 3/2008 | DeLeeuw et al. | 119/171 |
| 2006/0003948 | A1 * | 1/2006 | Krasutsky et al. | 514/28 |
| 2006/0134017 | A1 * | 6/2006 | Trivedi et al. | 424/50 |
| 2006/0134018 | A1 * | 6/2006 | Trivedi et al. | 424/50 |
| 2007/0132240 | A1 * | 6/2007 | Segal | 285/386 |

FOREIGN PATENT DOCUMENTS

| CA | 818375 | * | 5/1965 |
| WO | WO 9935120 | * | 7/1999 |
| WO | WO-0166066 | * | 9/2001 |

* cited by examiner

*Primary Examiner* — Alton Pryor
(74) *Attorney, Agent, or Firm* — Leffert Jay & Polglaze, P.A.

(57) ABSTRACT

A composition for and a method to kill nematodes, weeds, weed seeds and weed rhizomes in soils.

16 Claims, No Drawings

COMPOSITION AND METHOD FOR KILLING NEMATODES AND WEEDS IN SOILS

This invention relates to a method of applying compositions of mixtures thereof, a quaternary compound, dimethyl sulfoxide, ammonium lauryl sulfate, grapefruit peel and seed extracts and papain to kill nematodes and weeds in soils.

Methyl bromide has been used for decades around the world to kill nematodes and weeds. Methyl bromide has been banned by the Montreal Protocol ( ) signed by many developed and un-developed nations to stop the use of methyl bromide, as it has been proven to destroy the ozone layer surrounding the earth. This destruction is evident in the southern island of New Zealand where the skin cancer rate in humans has increased significantly.

The farmers in the United States of America continue to use methyl bromide even though the U.S.A. is a signatory of the Montreal Accord to stop using methyl bromide starting in 2001. Research conducted by U.S. Government scientists and universities up to now have produced no alternative to methyl bromide and it is still being used to grow tomatoes, melons and other crops.

Quaternary compounds have been used for decades as a cleaning compound and as a biocide. It has not proven itself or is currently used to kill nut sedge rhizomes. In fact, most homes in the U.S. have cleaning and deodorizing compounds that use quaternary compounds. These have been considered as safe to humans and the environment.

Ammonium lauryl sulfate is a well-known surfactant that has been used in soils to ameliorate the soil structure. Dimethyl sulfoxide is known to transfer through the cell wall of animals some compounds that are combined with and applied together to the skin of the animal. Papain is a well-known proteolytic enzyme that is used to tenderize meats. Grape fruit peel and seed extracts are currently sold around the world as a safe biocide and are used by humans.

Nematodes are very difficult to kill in the soil. Current nematicides used in the world are becoming useless, as these compounds do not reach their target in very compact soils. Nematodes are developing resistance to the nematicides that are currently used. The only compound that is proven to kill nut sedge rhizomes is methyl bromide. Methyl bromide is a good nematicide and a good killer of nut sedge rhizomes. It is not only very expensive, but is destroying the ozone layer above the earth.

There are no herbicides that are in use in U.S.A. that can kill nut sedge rhizomes found in California, Florida and other fruit growing states. This is the reason why the congress of the United States continues to extend the deadline to stop using the methyl bromide in U.S.A. because it kills not only nut sedge but also the nematodes.

We have discovered that using a quaternary compound mixed with a cell penetrating compound such as dimethyl sulfoxide and a soil diffusing agent such as ammonium lauryl sulfate, we could reach virtually all the nut sedge rhizomes in the soil and the nematodes in the soil that is being treated and then kill them successfully with the quaternary compound being aided by dimethyl sulfoxide to penetrate the rhizome of the nut sedge and the nematode's multi-cellular structure. We have also discovered that if papain is added to this mixture or if it replaces dimethyl sulfoxide, then the quaternary compound can become an effective nematode and nut sedge rhizome killer.

We have also discovered that the grapefruit peel and seed have compounds that act as very superior surfactants and can aid the quaternary compound to enter the nut sedge rhizome and the nematode and kill it. The most interesting result obtained by this invention is that it is not only killing the nematodes but is also killing the nut sedge rhizomes that cannot be killed by any herbicide except methyl bromide.

Therefore, as a result of this invention, as will be shown in the examples below, it has been discovered that it is not only a very effective nut sedge rhizome killer, but also a very effective nematicide. If used by the fruit producing community around the world, it will very effectively replace the methyl bromide still being used in developing countries and U.S.A. This can reduce the effects of methyl bromide on the ozone layer. Methyl bromide is a very strong carcinogen and is classified as dangerous by the E.P.A. Thus, replacing methyl bromide by the compositions in this invention can also reduce the risk to workers in the farms currently using methyl bromide.

EXAMPLE 1

In this example, various compounds of the invention were mixed in various compositions to ascertain if the compounds are synergistic, and if so how well they work in combinations Composition A:
  N,N-dibutyl-N-benzyl benzammonium chloride 25% by weight.
  N-butyl,N-hexyl-n-benzyl benzammonium chloride 25% by weight.
  Dimethyl sulfoxide 5% by weight.
  Ammonium lauryl sulfate 2% by weight.
  Papain 0.25% by weight.
  Grapefruit peel and seed extracts 15% by weight.
  Water to make up to 100% by weight.

Composition B:
  N,N-dibutyl-N-benzyl benzammonium chloride 25% by weight.
  N-butyl, N-hexyl-n-benzyl benzammonium chloride 25% by weight.
  Di methyl sulfoxide 5% by weight.
  Ammonium lauryl sulfate 2% by weight.
  Papain 0.25% by weight.
  Water to make up to 100% by weight.

Composition C:
  N,Ndibutyl-N-benzyl benzammonium chloride. 25% by weight.
  N-butyl,N-hexyl-n-benzyl benzammonium chloride 25% by weight.
  Ammonium laurel sulfate 2% by weight.
  Water to make up to 100% by weight.

Composition D:
  N,Ndibutyl-N-benzyl benzammonium chloride. 25% by weight.
  N-butyl,N-hexyl-n-benzyl benzammonium chloride 25% by weight.
  Water to make up to 100% by weight.

Field trials were conducted in Florida where tomatoes are grown under a plastic mulch and an irrigation system, called "T" tapes, which is used to irrigate the crop under the plastic mulch. Design of the experiment were three rows of a standard methyl bromide applications as the smallest replication. Four such sets of three rows were used as replicated applications. There was a zero treatment. Methyl bromide gas used at a 400 pounds per acre basis as the control and the compositions A, B, C. and D were used at a 5 liters per acre basis. Composition A was injected through the "T" tape one day after methyl bromide was injected.

The plants growing in the middle rows only of these three rows, were used to collect data. In the middle rows, 14 plants were randomly selected for measuring. The height of the plants were collected at 30 days. Starting at fruit harvest, fruits collected from these 14 plants were cumulatively added to give the total production data. At the end of harvest these plants were carefully dug up and roots carefully washed to weigh the total roots and also measure the degree of infection in the roots. Soil samples were also collected from the holes where the plants were dug up and analyzed for soil nematode population. Finally, all nut sedge plants that came through the plastic mulch in the entire 150-yard middle rows were counted as a "strike", a degree of insufficient kill of the rhizomes. Results obtained in this experiment is shown in Table I

TABLE I

| Treatment | Height at 30 Days | Production Per Plant | Soil Nematode | Weight of Roots | Infection in Roots | Live nut sedge in 150 yards |
|---|---|---|---|---|---|---|
| Methyl Bromide | 2.6 feet | 16 lbs. | 700/10 gr | 165 gr. | zero | 12/150 strikes". |
| Comp A. | 2.9 feet | 18 lbs. | 826/10 gr | 196 gr. | zero | 12/150 strikes". |
| Comp B. | 2.7 feet | 16.6 lbs. | 850/10 gr | 182 gr. | zero | 15/150 strikes". |
| Comp C. | 2.6 feet | 16.1 lbs. | 876/10 gr | 175 gr. | zero | 16/150 strikes". |
| Comp D. | 2.5 feet | 15.2 lbs. | 906/10 gr | 168 gr. | trace | 17/150 strikes". |

*Nut sedge shoot piercing through and growing through the plastic mulch

Discussion: Methyl Bromide had the same efficacy in controlling the weeds as composition A. On nematode control in the soil it was superior to compositions A, B, C and D. But methyl bromide is well known to also have slight residual effects on plants that are planted in these treated rows, as methyl bromide does not totally degrade in the 20-day post injection interval needed for planting the tomatoes. Compositions A through D seem to have biodegraded faster than the methyl bromide, as shown in production and root growth, though not statistically significant. The results also showed that the full mix of all the compounds performed better than when some of the compounds were removed, as in compositions B, C and D.

EXAMPLE II

In this experiment, methyl bromide was applied at full dose of 400 pounds per acre of the gas and the treatments used 200 pounds of methyl bromide per acre alone and with 5 liters of composition A per acre, 100 pounds of methyl bromide alone and with composition A at 5 liters per acre, 50 pounds of methyl bromide with 5 liters of composition A and the last treatment of 5 liters of composition A per acre by itself. Tomatoes were planted 20 days after methyl bromide was injected under the plastic mulch. Composition A was injected through the "T" tape one day after methyl bromide was injected. The design of Experiment II was the same as in Experiment I, and the data collected were as in the Experiment I. The results of this experiment are shown in Table II.

Results with Experiment II show that the compositions without any methyl bromide were sufficient to control the nematodes and weeds. The exercise to discover if any methyl bromide was needed to supplement the compositions of the invention to control nematodes and weeds proved unnecessary.

EXPERIMENT III

In this experiment, pickles were grown in second use plastic mulch, where in normal commercial practice, growers do not fumigate with methyl bromide. Methyl bromide is too expensive and the growers believe that the first use plastic, where methyl bromide had been used in the soil, the soil would still be free of nematodes and nut sedge rhizomes. The grower takes a calculated risk in planting plants such as pickles or green peppers in these rows in the second-generation plastic mulch.

Under these conditions, Composition A was tested at 5 liters and 3 liters per acre applied through the "T" tape 15 days pre-planting. The controls were the second-generation plastic with no methyl bromide or any other fumigant applied prior to planting. Data were collected similar to Experiment I. The results of this experiment are shown in Table III.

TABLE II

| Treatment | Height at 30 Days | Production Per Plant | Soil Nematode | Weight of Roots | Infection in Roots | Live nut sedge in 150 yards |
|---|---|---|---|---|---|---|
| M.B. (400 lbs) | 3 ft. | 8.6 lbs. | zero | 170 gr. | zero | 7 strikes |
| M.B. 200 lbs. | 2.7 ft. | 6.1 lbs. | 1056/10 gr. | 120 gr. | slight | 18 strikes |
| M.B. 200 lbs. + comp A. 5 lts. | 3.2 ft. | 8.9 lbs. | zero | 186 gr. | zero | 8 strikes |
| M.B. 100 lbs. | 2.2 ft. | 5.1 lbs. | 2200/10 gr. | 90 gr. | high | 28 strikes |
| M.B. 100 lbs. + comp A. 5 lts. | 3.3 ft. | 9.1 lbs. | zero | 180 gr. | zero | 7 strikes |
| M.B. 50 lbs. | 2 ft. | 4 lbs. | 16,000 | 60 | high | 38 strikes |
| M.B. 50 lbs + comp A. 5 lts. | 3.1 ft. | 9 lbs. | zero | 182 | zero | 8 strikes |
| Comp A. 5 lts. | 3.4 ft. | 9.5 lbs. | zero | 196 | zero | 9 strikes |

TABLE III

| Treatment | Size of Plant | Production Per Plant | Soil Nematode | Weight of Roots | Infection in Roots | Live nut sedge sedge |
| --- | --- | --- | --- | --- | --- | --- |
| None | small | 1.5 pickles | 29,000 per 10 gr. | 37 gr. | high | 21 strikes |
| Comp A at 5 qts. | large | 2.5 pickles | zero | 89 gr. | zero | 6 strikes |
| Comp A at 3 qts. | large | 2.4 pickles | 606 per 10 gr. | 76 gr. | zero | 8 strikes |

The results in this experiment showed that the nematode population in the Florida soils increase so much that when pickles are grown in the second generation or second use plastic mulch, the nematodes will attack the roots of the pickles grown in this mulch without any nematicide and reduce production significantly.

It also showed that when Composition A was used at 5 and 3 liters, the nematode attack was zero and the root mass was high and the production was also significantly higher than the untreated. It is therefore apparent that the compositions can kill nematodes and weeds, specially the most difficult weed, the nut sedge rhizome.

What is claimed:

1. A nematicide and herbicide composition comprising:
   a quaternary compound;
   dimethyl sulfoxide;
   ammonium lauryl sulfate;
   grapefruit peel and seed extracts; and
   papain.

2. The nematicide and herbicide composition according to claim 1, wherein the grapefruit peel and seed extracts are composed mainly of naringin, isonaringin and hesperidin.

3. The nematicide and herbicide composition according to claim 1, wherein the papain is a proteolytic enzyme produced by the papaya plant.

4. The nematicide and herbicide composition according to claim 1, wherein the quaternary compound comprises an alkyl ammonium compound.

5. The nematicide and herbicide composition according to claim 1, wherein the quaternary compound comprises an N,N-dibutyl-N-benzyl benzammonium chloride.

6. The nematicide and herbicide composition according to claim 1, wherein the quaternary compound comprises an N-butyl, N-hexyl-n-benzyl benzammonium chloride.

7. The nematicide and herbicide composition according to claim 1, wherein the quaternary compound comprises a dimethylbenzyl ammonium saccharinate.

8. The nematicide and herbicide composition according to claim 1, wherein the quaternary compound comprises a quaternary ammonium chloride.

9. The nematicide and herbicide composition according to claim 1 wherein the quaternary compound is from about 1% by weight to about 85% by weight of the total composition; the dimethyl sulfoxide is from about 0.5% by weight to about 20% by weight of the total composition; the ammonium lauryl sulfate is from 1% by weight to about 20% by weight of the total composition, the grape fruit peel and seed extracts is from about 1% by weight to about 75% by weight of the total composition, the papain is from 0.25% by weight to 2.5% by weight of the total composition.

10. A method of applying the compositions according to claim 1 into soil that is treated prior to planting seeds, seedlings or plants.

11. A method of applying the compositions according to claim 1 comprising shanking the compositions into soil and immediately covered by a plastic cover or mulch.

12. A method of applying the compositions according to claim 1 comprising injecting the compositions through an irrigation system incorporated under plastic mulch where soil is being treated.

13. A method of applying the compositions according to claim 1 comprising applying the compositions applied to soil through an overhead irrigation or sprinkler system.

14. A nematicide and herbicide composition comprising:
    a quaternary compound;
    dimethyl sulfoxide;
    ammonium lauryl sulfate; and
    grapefruit peel and seed extracts.

15. The nematicide and herbicide composition according to claim 14, wherein the quaternary compound comprises an alkyl ammonium compound.

16. The nematicide and herbicide composition according to claim 14, wherein the quaternary compound comprises a quaternary ammonium chloride.

* * * * *